United States Patent [19]

Kuo et al.

[11] Patent Number: 5,565,204
[45] Date of Patent: Oct. 15, 1996

[54] PNEUMOCOCCAL POLYSACCHARIDE-RECOMBINANT PNEUMOLYSIN CONJUGATE VACCINES FOR IMMUNIZATION AGAINST PNEUMOCOCCAL INFECTIONS

[75] Inventors: Joseph S.-C. Kuo, Tappan, N.Y.; Heesoo K. Ree, Kyongbuk, Rep. of Korea

[73] Assignee: American Cyanamid Company, Wayne, N.J.

[21] Appl. No.: 295,305

[22] Filed: Aug. 24, 1994

[51] Int. Cl.$^6$ .................. A61K 39/09; A61K 39/00; A61K 39/38; A61K 39/385
[52] U.S. Cl. .................. 424/244.1; 424/184.1; 424/193.1; 424/197.11; 536/105; 536/126
[58] Field of Search .................. 424/197.11, 184.1, 424/244.1, 193.1; 536/105, 126

[56] References Cited

U.S. PATENT DOCUMENTS

| | | | |
|---|---|---|---|
| 4,242,501 | 12/1980 | Cano et al. | 536/1 |
| 4,356,170 | 10/1982 | Jennings et al. | 424/92 |
| 4,673,574 | 6/1987 | Anderson | 424/92 |
| 4,686,102 | 8/1987 | Ritchey et al. | 424/92 |
| 4,761,283 | 8/1988 | Anderson | 424/92 |
| 4,830,852 | 5/1989 | Marburg et al. | 424/85.8 |
| 4,902,506 | 2/1990 | Anderson et al. | 424/92 |
| 5,192,540 | 3/1993 | Kuo et al. | 424/92 |
| 5,306,492 | 4/1994 | Porro | 424/88 |
| 5,360,897 | 11/1994 | Anderson et al. | 530/403 |
| 5,371,197 | 12/1994 | Marburg et al. | 530/404 |
| 5,445,817 | 8/1995 | Schneerson et al. | 424/194.1 |

FOREIGN PATENT DOCUMENTS

| | | | |
|---|---|---|---|
| 497525 | 8/1992 | European Pat. Off. | A61K 39/385 |
| 9006950 | 6/1990 | WIPO | C07K 13/00 |
| WO91/04049 | 4/1991 | WIPO | A61K 39/09 |

OTHER PUBLICATIONS

Phillips, J. R., et al., Carbohydrate Res., 121, 243–255 (1983).
Paton, J. C., et al., Infection & Immunity, 59, 2297–2304 (1991).
Boulnois, G. J., J. Gen. Microbiol., 138, 249–259 (1992).
Walker et al., 1987, Molecular cloning, characterization, and complete nucleotide sequence of the gene pneumolysin, the sulfhydryl–activated toxin of Streptococcus pneumoniae, Infection and Immunity, 55(5):1184–1189.
Paton et al., 1983, Effect of immunization with pneumolysin on survival time of mice challenged with Streptococcus pneumoniae, Infection and Immunity, 40(2):548–552.
Paton et al., 1986, Cloning and expression of Escherichia coli of the Streptococcus pneumoniae gene encoding pneumolysin, Infection and Immunity, 54(1):50–55.
Rubins et al., 1992, Toxicity of Pneumolysin . . . Inf & Imm. 60(5):1740–46.
Paton, J. C., et al., Ann. Rev. Microbiol., 47, 89–115 (1993).
Lee, C.-J., et al., Vaccine, 12, 875–878 (1994).
Lee et al. 1994. Protection of infant mice from challenge with Streptococcus . . . Vaccine 12(10):875–878.
Lee et al. 1994. Pneumococcal infection and immunization in children. Critical Reviews in Microbiol. 20(1):1–12.

Primary Examiner—James C. Housel
Assistant Examiner—N. M. Minnifield
Attorney, Agent, or Firm—Alan M. Gordon

[57] ABSTRACT

Immunogenic polysaccharide-protein conjugates are generated which have an oxidized polysaccharide derived from the capsular polysaccharide of *Streptococcal pneumniae* and the pneumolysin protein of *S. pneumoniae* which is expressed recombinantly. The pneumolysin is not toxoided prior to conjugation with said oxidized polysaccharide. The immunogenic conjugates are used as vaccines to elicit antibody responses to the capsular polysaccharide of *S. pneumoniae* and to recombinant pneumolysin, and to immunize against *S. pneumoniae*-caused disease.

16 Claims, 4 Drawing Sheets

PNEUMOCOCCAL POLYSACCHARIDE-RECOMBINANT PNEUMOLYSIN CONJUGATE VACCINES FOR IMMUNIZATION AGAINST PNEUMOCOCCAL INFECTIONS

FIELD OF THE INVENTION

This invention relates to an immunogenic polysaccharide-protein conjugate comprising an oxidized polysaccharide derived from the capsular polysaccharide of Streptococcal pneumoniae and the pneumolysin protein of S. pneumoniae which is expressed recombinantly, where said pneumolysin is not toxoided prior to conjugation with said oxidized polysaccharide.

BACKGROUND OF THE INVENTION

Streptococcal pneumoniae (S. pneumoniae) is the most common pathogenic cause of bacterial pneumonia, and is also one of the major causes of bacterial otitis media (middle ear infections), meningitis and bacteremia. There are at least 83 types of the pneumococcal organism, each with a different chemical structure of the capsular polysaccharide. The capsular polysaccharide is the principal virulence factor of the pneumococcus and induces an antibody response in adults. Currently, a 23-polyvalent polysaccharide vaccine (such as Pnu-Imune®, American Cyanamid Company, Wayne, N.J.) is available for adults and children over two years of age. Preparation of this purified pneumococcal polysaccharide vaccine is disclosed in U.S. Pat. Nos. 4,242,501, 4,221,906 and 4,686,102 (Bibliography entries 1,2,3). However, children less than two years of age do not induce a good immune response to this type of vaccine.

To modify the immunological characteristics and enhance the immunogenicity of the polysaccharide in children younger than two years of age, the polysaccharide has been covalently conjugated to a protein carrier to form a polysaccharide-protein conjugate. Preparation of the conjugate polysaccharide-protein conjugate vaccine is disclosed in U.S. Pat. No. 4,673,574 (4). The patent relates to the preparation of immunogenic conjugates comprising a polysaccharide fragment derived from the capsular polymer of S. pneumoniae or Haemophilus influenzae type b containing a reducing group(s) and a bacterial toxin or toxoid, specifically nontoxic diphtheria toxin (such as $CRM_{197}$) as a protein carrier.

An effort to enhance the immunogenicity of a polysaccharide has been reported in which site-directed mutagenesis was used to generate non-toxic toxoids of a toxic S. pneumoniae protein, pneumolysin. The resulting mutant pneumolysin toxoids were conjugated to a Type 19F pneumococcal capsular polysaccharide through the use of linker or spacer, 6-aminocaproic acid. The conjugate enhanced the immunogenicity of the Type 19F polysaccharide moiety compared with that of the unconjugated polysaccharide (5,6). A follow-up study indicated that untoxoided native pneumolysin is unsuitable for inclusion in a vaccine because of its toxicity (7).

However, despite these and other efforts, there is no efficacious vaccine against S. pneumoniae for children less than two years of age. Thus, there is a need for such a vaccine.

SUMMARY OF THE INVENTION

It is an object of this invention to provide immunogenic polysaccharide-protein conjugates comprising an oxidized polysaccharide derived from the capsular polysaccharide of S. pneumoniae, and a protein carrier, the pneumolysin protein of S. pneumoniae which is expressed recombinantly, where said pneumolysin is not toxoided prior to conjugation with said oxidized polysaccharide. The pneumolysin is not toxoided; nonetheless, the resulting conjugate has greatly reduced toxicity.

In one embodiment of this invention, the oxidized polysaccharide is conjugated directly to the pneumolysin protein. In other embodiment of this invention, the pneumolysin protein is first linked to a spacer and is then conjugated to the oxidized polysaccharide.

It is a further object of this invention to use these conjugates as vaccines. These vaccines are useful in eliciting an antibody response to the capsular polysaccharide of S. pneumoniae in warm-blooded animals.

It is still another object of this invention to use these vaccines to immunize against S. pneumoniae-caused disease in warm-blooded animals, by administering these vaccines in an immunogenic amount by intramuscular or subcutaneous injection.

In an additional embodiment of this invention, the vaccine comprises a mixture of at least two immunogenic conjugates with oxidized polysaccharides derived from capsular polysaccharides of different types of S. pneumoniae.

In a further aspect of this invention, the Type 18C polysaccharide of S. pneumoniae is treated with mild acid to partially depolymerize the polysaccharide prior to oxidation, in order that conjugation with recombinant pneumolysin ("rPL") can be carried out successfully.

The conjugate vaccines of this invention are highly immunogenic in warm-blooded animals. The vaccines elicit antibodies to both the polysaccharide and the protein, recombinant pneumolysin.

The conjugates of this invention have distinct advantages over those described previously, in that the protein carrier is derived from pneumolysin, which has been reported to be a virulence factor in pneumococcal infections (8). The conjugate vaccines of this invention elicit antibodies to both the polysaccharide and the pneumolysin (both of which are virulence factors), and confer immunity to the diseases caused by S. pneumoniae. The conjugates induce antibodies to pneumolysin which are capable of neutralizing the hemolytic and cytotoxic activities of the toxin without the requirement for a spacer or linker described previously (5,6), although such spacers can be used. While site-specific mutagenesis is not required for the production of a pneumolysin which retains its conformation while being rendered non-toxic, such mutagenesis is within the scope of this invention.

In addition to permitting the vaccines to confer immunity in children less than two years of age, the carrier protein, rPL, may itself confer immunity and not merely act as a carrier for the oxidized polysaccharide. Finally, because the conjugate vaccines do not include the use of the entire S. pneumoniae organism, administration of the vaccines will not induce S. pneumoniae-caused disease.

DETAILED DESCRIPTION OF THE INVENTION

Figure 1:
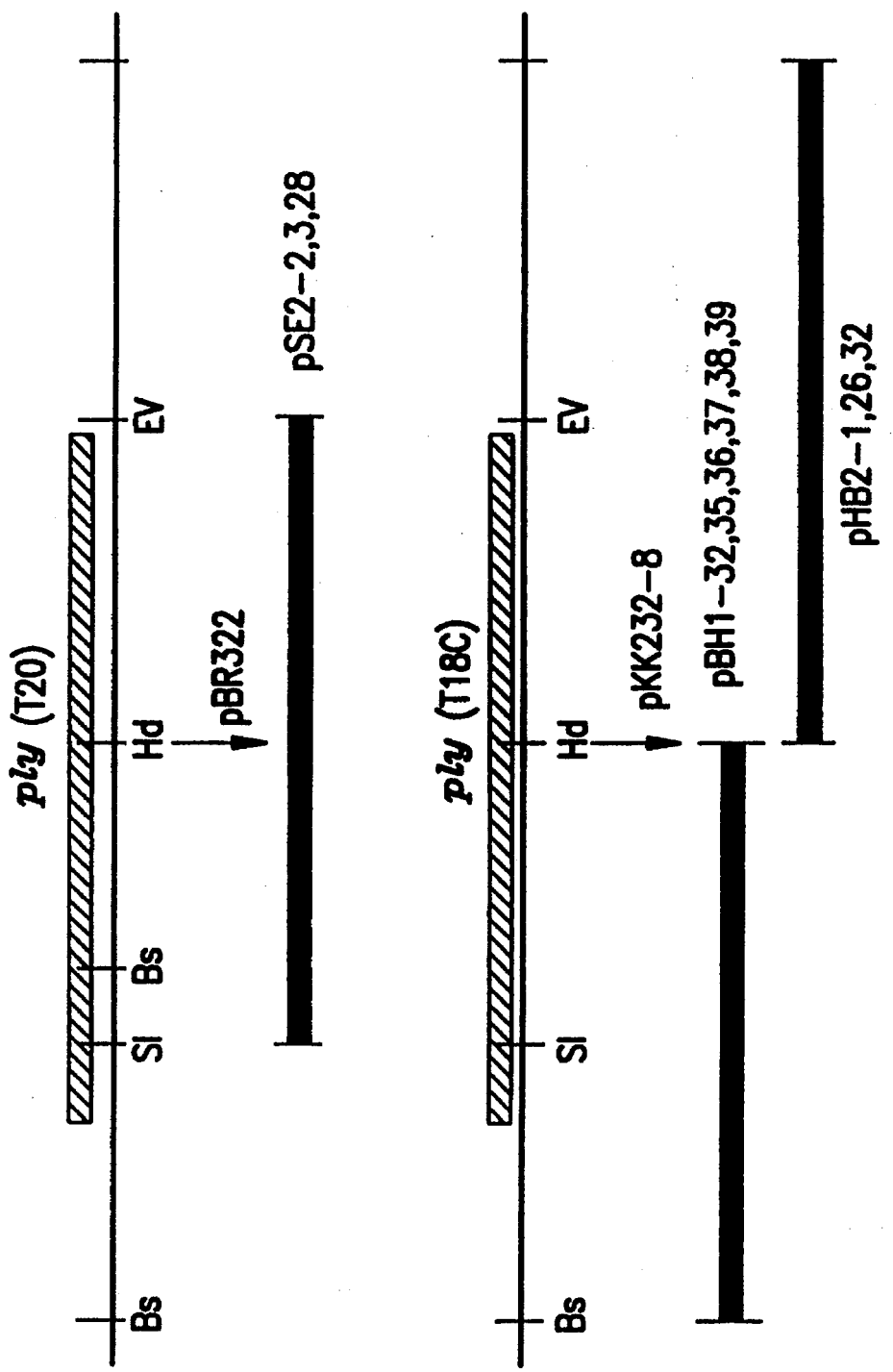
FIG. 1 depicts a physical map of the clones covering the pneumolysin gene (ply) from S. pneumoniae Types 18C and 20. Restriction sites are abbreviated as follows: Bs=BstYI, S1=SalI, Hd=HindIII, EV=EcoRV.

Pneumolysin, a sulfhydryl-activated hemolytic toxin 471 residues in length, is produced by all types of S. pneumoniae and is considered a putative virulence factor in pneumococcal infections. This toxin has a molecular weight of approximately 53,000 daltons (53 kD). Mice and rats injected with inactivated pneumolysin exhibit enhanced survival when challenged with live S. pneumoniae (9,10). Therefore, pneumolysin is a potential vaccine candidate and, as shown in this invention, is a useful protein carrier for the preparation of a conjugate vaccine. Since native pneumolysin is produced at a low level in S. pneumoniae, the construction of a recombinant E. coli that over-expresses rPL is undertaken. The pneumolysin genes have already been cloned, sequenced and expressed in E. coli from S. pneumoniae types 1 (11), 2 (12) and 19F (13), as well as in Bacillus subtilis (13A). Pneumolysin is not secreted by the S. pneumoniae bacterium, apparently because of the lack of a signal sequence (12).

Among the aspects of this invention exemplified below are processes including cloning of the pneumolysin gene from S. pneumoniae and the several fold over-expression of the pneumolysin in E. coli as a fusion protein using the glutathione S-transferase (GST) gene fusion system and purification of the 53 kilodalton (kD) rPL using affinity chromatography with a glutathione-agarose column and cleavage of GST in the fusion protein containing GST-rPL by using a site-specific protease, thrombin. The amino acid composition, terminal amino acid sequence and immunological reactivities of the rPL are determined. The rPL obtained in this manner is the same as the native protein, except that after the GST of the fusion protein is cleaved off, two additional amino acids are present at the amino-terminus of rPL.

As detailed in Example 1 below, expression vectors containing the pneumolysin gene from Type 18C or a hybrid pneumolysin gene from a fusion of portions of the gene from Type 18C and Type 20 are prepared and inserted into E. coli hosts. Other types of S. pneumoniae are also suitable sources of the pneumolysin gene. Other conventional host cells are suitable for expression of the rPL.

Samples of the E. coli strain SCS1 carrying the recombinant plasmid pGEX-PL 18C/20 were deposited by Applicants with the American Type Culture Collection, 12301 Parklawn Drive, Rockville, Md. 20852, U.S.A., and have been assigned ATCC accession number 69654.

Samples of the E. coli strain SCS1 carrying the recombinant plasmid pGEX-PL 18C/20 were deposited by Applicants with the American Type Culture Collection, 12301 Parklawn Drive, Rockville, Md. 20852, U.S.A., and have been assigned ATCC accession number 69655.

The material deposited with the ATCC can also be used in conjunction with conventional genetic engineering technology to regenerate the native pneuomolysin protein, which lacks the additional glycine and serine residues which remain after thrombin cleavage at the N-terminus.

The capsular polysaccharides of various pneumococcal types used in this invention have been described in commonly-assigned U.S. Pat. Nos. 4,242,501 and 4,686,102 (1,3), which are incorporated by reference. The purified pneumococcal polysaccharides so obtained have a relatively high molecular size, with more than 50% having an elution coefficient ($K_{av}$) value less than 0.3 on a column of Sepharose™ CL-4B (Pharmacia LKB Biotechnology, Piscataway, N.J.). This value corresponds to a molecular weight greater than $6 \times 10^5$ daltons.

In its native form, the polysaccharides from pneumococcal organisms do not contain reactive reducing groups. In order to create each reactive polysaccharide containing reducing groups, the polysaccharide is partially hydrolyzed with controlled amounts of sodium periodate to produce reducing groups by cleavage of the cis-vicinal hydroxyl group of the polysaccharide by oxidizing with a periodate, to generate aldehyde functions following the process of Parikh, et al. (14). The purified pneumococcal polysaccharides are treated in the dark with 0.2–50 mM of sodium periodate at 4° C. or at room temperature for various lengths of time. In a preferred embodiment, the polysaccharide is treated at pH 4.0–5.0. The use of sodium periodate is preferred.

Another aspect of this invention is a process for the preparation of the oxidized pneumococcal polysaccharides, such as Types 6B, 14 and 18C ([O]6B, [O]14 and [O]18C), to create reactive groups of the polysaccharide by weak acidic or oxidative cleavage using periodate.

After oxidation, the oxidized polysaccharide ("[O]PS") is then dialyzed extensively against pyrogen-free water to remove small molecular size materials. Alternatively, a gel filtration column such as Sepharose™ CL-4B may be used for the purification of the [O]PS. When a gel filtration column is used, the fractions are assayed for the presence of [O]PS by the phenol-sulfuric acid calorimetric method using the purified corresponding polysaccharide as the standard (15). The purified product is then recovered by concentrating and freeze-drying. The resulting [O]PS has a chain length of about 15–800 monomeric units.

A novel method is used to create the reactive groups in Type 18C: The polysaccharide is partially depolymerized, cleaved to produce an intermediate size molecule, and then oxidized.

If the oxidation is carried out in the absence of partial depolymerization, an unusable gel-like material is obtained. To overcome this problem, the Type 18C polysaccharide is first partially depolymerized by mild acid, such as acetic acid treatment, to reduce it to a molecular size of approximately 10,000–600,000 (Kay on Sepharose™ CL-4B column of 0.3–0.7). Only then is the Type 18C polysaccharide subjected to periodate oxidation as described above to create functional reducing groups. When conjugated to rPL as described below, the product is in a form suitable for vaccine use.

The [O]PS is coupled with the rPL as a protein carrier using either direct or indirect conjugation. For direct conjugation, the [O]PS is conjugated to the rPL using cyanoborohydride for reductive amination by conventional means.

The functional aldehyde groups in the [O]PS are reacted with rPL, which contains amino groups (particularly lysine groups) to form a Schiff base. In the presence of a mild selective reducing agent such as cyanoborohydride, a stable, covalently-bounded conjugate is formed. The reaction is preferably carried out at pH 5 to 9. The methodology for the coupling of [O]PS to a protein using has been described by Parikh et al. (14) and Schwartz and Gray (16).

The [O]PS of the pneumococcal type 6B, 14 or 18C (concentration 1–10 mg/ml) is mixed with rPL (concentration 1–10mg/ml) in 0.2M potassium phosphate buffer or sodium phosphate buffer (pH 6.0 8.0) at room temperature or 37° C.

After 30 minutes of incubation with gentle mixing, 0.1–2.0 mM of sodium cyanoborohydride is added. This mixture is incubated at 25–37° C. with gentle mixing for 1–8 days to form the [O]PS-rPL conjugate. The conjugate is purified on a gel filtration column such as Sepharose™ CL-4B. Fractions are assayed for protein by the Bradford method with the Bio-Rad protein assay reagent (17), using bovine serum albumin as the standard, and assayed for [O]PS as described previously (15). The fractions which contain the conjugate are pooled, dialyzed and diafiltered and/or lyophilized.

Alternatively, the rPL is first linked to a spacer prior to conjugation with the [O]PS. Examples of such spacers are adipic acid dihydrazide (ADH) and 6-aminocaproic acid. ADH is the preferred spacer.

The conjugates which have been processed in accordance with this invention are preferably used in the preparation of vaccines to confer protection of warm-blooded animals against *S. pneumoniae* caused disease. The hemolytic activity (toxicity) of the rPL is greatly reduced when it is conjugated with the [O]PS (alone or with a spacer), as compared to pneumolysin administered alone.

The conjugates may be added to immunologically acceptable diluents or carriers in the conventional manner to prepare injectable liquid solutions or suspensions. In addition, the conjugates may be bound to aluminum hydroxide, aluminum phosphate (alum) or other pharmaceutically acceptable adjuvants, such as QS-21 (18), monophosphoryl lipid A and deacylated monophosphoryl lipid A.

For instance, to prepare a conjugate vaccine containing [O]PS and rPL, or a vaccine containing a mixture of several conjugates,1 each containing rPn and a different type of [O]PS, the conjugate preparation(s) is suspended in sodium phosphate-buffered saline ("PBS") (pH 7.0–8.0) at concentrations of 1–100 μg of the polysaccharide per ml.

The conjugate vaccines of this invention are administered by injection in a conventional manner, such as subcutaneous, intraperitoneal or intramuscular injection into warm-blooded animals to induce an active immune response for protection against systemic infection caused by the pathogen *S. pneumoniae*. The dosage to be administered is determined by means known to those skilled in the art. Protection may be conferred by a single dose of vaccine, or may require the administration of several booster doses.

It is noteworthy that, although rPL is not itself protective, mice receiving rPL alone live longer than mice receiving [O]18C polysaccharide alone. Thus, the protective effect of the conjugate appears to be due both to rPL acting as a carrier for the [O]PS, as well as a function of the rPL itself.

In order that this invention may be better understood, the following examples are set forth. The examples are for the purpose of illustration only and are not to be construed as limiting the scope of the invention.

EXAMPLES

Example 1

Cloning and Expression of rPL Gene

Construction of an Expression Vector Containing a Hybrid Type 18C/20 rPL Gene

A fusion ply gene is constructed from types 18C and 20, subcloned into an appropriate expression vector and a hybrid rPL is expressed. The 3' end of the gene is obtained from type 20, while the 5' end of the gene is obtained from type 18C.

In order to determine the appropriate restriction sites for the cloning of the Type 20 ply gene, Southern blots are carried out using a 3' end-labelled oligonucleotide probe (designated PL20), which hybridizes to the highly conserved region among sulfhydryl-activated hemolysins (nucleotides 1484–1503; 12). The probe is labelled with either biotin or digoxigenin. The 1.3 kb SalI-EcoRV fragment is identified as comprising most of the ply gene, except for the 5' end of the gene. This 1.3 kb fragment is inserted into SalI and EcoRV sites in pBR322 (Boehringer Mannheim Co., Indianapolis, Ill.). Competent cells of *E. coli* strain SCS1 (Stratagene, LaJolla, Calif.) are used as a host. Ampicillin-resistant and tetracycline-sensitive transformants are screened by colony hybridization using the PL20 probe. Three identical recombinants, designated pSE2-2, 3 and 28, are isolated (FIG. 1).

The SalI-EcoRV fragment of pSE2 is excised and inserted into the SalI and SmaI sites of pUC19 (New England Biolabs, Beverly, Mass.). Ampicillin-resistant, lactose-negative (colorless colonies on X-gal [5-bromo-4-chloro-3-indolyl-β-D-galactopyranoside] containing plates when induced by isopropyl-β-D-thiogalactopyranoside ("IPTG")) transformants are screened by restriction analysis. One of the positive recombinants is designated pSE3-5.

Because there are no restriction sites suitable for the cloning of the 5' end of the ply gene from Type 20, Southern blots are performed with the genomic DNA from Type 18C. A 1.3 kb SalI-EcoRV fragment from pSE2-2, which is labelled by mixed10 primer labelling, is used as a probe. A 2.8 kb BstYI fragment is identified as containing the complete ply gene, together with the 5' and 3' flanking regions. This BstYI fragment is digested with HindIII, and inserted into the BamHI and HindIII sites of a promoter-selection vector, pKK232-8 (19; Pharmacia). *E. coli* strain SCS1 is used as a host.

To select transformants containing the promoter of the ply gene, ampicillin-resistant (100 μg/ml) and chloramphenicol-resistant (5 μg/ml) transformants are screened by restriction analysis and Southern blotting. Six identical recombinants, designated pBH1-32, 35, 36, 37, 38 and 39, are found to contain a 1 kb BstYI-HindIII fragment spanning the 5' upstream noncoding region and the 5' region of the ply gene from Type 18C (FIG. 1).

Then, in order to produce a functional recombinant protein, the pneumococcal DNA fragments cloned from Types 18C and 20 described above are fused to construct a hybrid ply gene in the plasmid pGEX-2T (Pharmacia) using the glutathione-S-transferase fusion protein system (20).

Polymerase Chain Reaction (PCR) is performed to facilitate the subcloning of the 5' end of the gene. Two primers are synthesized: a sense primer at the beginning of the coding sequence with a BamHI site introduced just upstream of the initiation codon to facilitate cloning (nucleotides 208–231; 12); and an antisense primer which hybridizes to the area covering the unique EcoRI site within the gene (nucleotides 709–733; 12). The 0.7 kb BstYI-EcoRI fragment from pBH1-37 (Type 18C) serves as a template to be amplified by Vent™ DNA polymerase (New England Biolabs, Beverly, Mass.), thereby generating 0.5 kb fragments.

PCR experiments are performed as follows: DNA is denatured at 95° C. for 5 minutes prior to the addition of Vent™ DNA polymerase, and 30 cycles of denaturation (95° C. for 30 seconds), annealing (50° C. for 30 seconds) and polymerization (72° C. for 1.5 minutes) are carried out.

Figure 2:
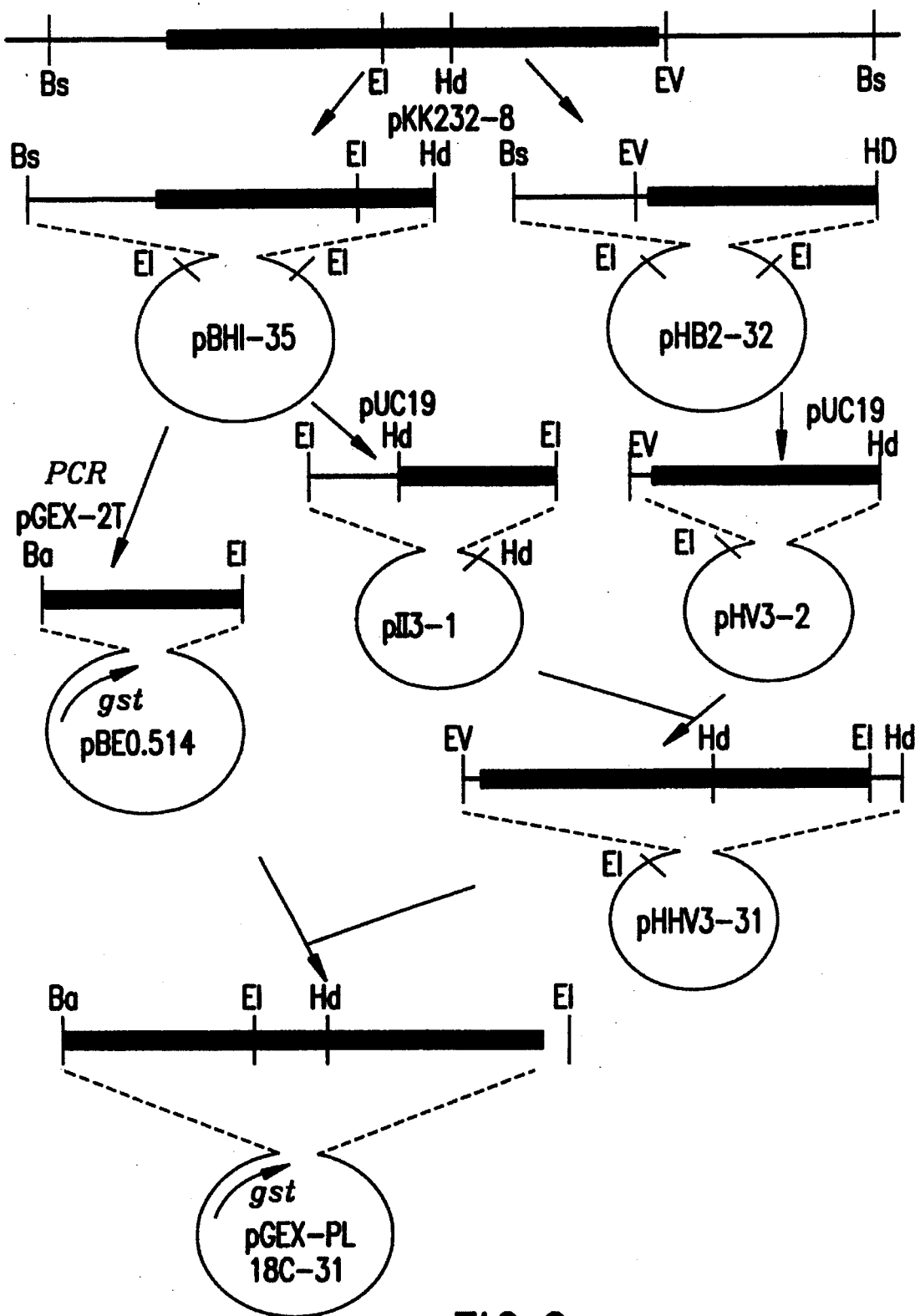
FIG. 2 depicts the scheme for the subcloning of the ply gene from S. pneumoniae Type 18C into an expression vector, pGEX-2T, to generate pGEX-PL 18C-31. Restriction sites are abbreviated as follows: EI=EcoRI, Bs=BstYI, Hd=HindIII, EV=EcoRV, BH=BamHI.

Amplified DNA fragments are digested with BamHI and EcoRI and then inserted into the BamHI and EcoRI sites in pGEX-2T. Randomly-picked ampicillin-resistant transformants are tested for the presence of the desired insert by restriction analysis. A recombinant designated pBE0,514 is identified as positive (FIG. 2). Next, the 1.0 kb EcoRI (a unique site within the gene)-EcoRI (derived from the pUC19 vector, New England Biolabs) fragment from pSE3-5 (Type 20) is inserted downstream of the amplified DNA within pBE0,514.

Positive recombinants are identified by a rabbit erythrocyte overlay (12), which is conducted as follows. Ampicillin-resistant transformants on LB agar plates are overlaid with 5 ml of 2.5% rabbit blood cells (in 0.7% molten agar in PBS containing 1 mM IPTG and 1 mMDTT) and incubated at 37° C. for three hours. Colonies carrying recombinant plasmids show circular zones of hemolysis.

Four individual colonies (pGEX-PL 18C/20-1, 2, 3 and 11) show circular zones of hemolysis. Restriction analyses confirm the presence of the complete ply gene which is fused to the 3' end of the gst gene.

Construction of an Expression Vector Containing Type 18C rPL Gene

As described above, digestion of the 2.8 kb BstYI fragment of Type 18C chromosomal DNA with HindIII produces a 1 kb fragment spanning the 5' upstream noncoding region and the 5' region of the ply gene from Type 18C. The digestion also produces a 1.8 kb fragment spanning the 3' region of the ply gene and the 3' noncoding region (FIG. 1), as identified by colony hybridization. Screening of the ampicillin-resistant and chloramphenicol-sensitive transformants identifies three identical recombinants designated pHB2-1, 26 and 32.

Construction of the complete ply gene from Type 18C in pGEX-2T requires the ligation of three fragments. Due to the shortage of restriction sites to be used in subcloning, a series of cloning steps is performed.

First, pHB2-32 is digested with HindIII and EcoRV to produce a 0.7 kb fragment. This fragment is inserted into pUC19 to generate three recombinants designated pHV3-2, 4 and 6. Second, pBH1-35 is digested with EcoRI to produce a 0.5 kb fragment which is inserted into pUC19 to generate five recombinants designated pII3-1, 2, 3, 4 and 5. Third, pII3-1 and either pHV3-2 or 6 are digested with HindIII. Fourth, the cloning of the 0.3 kb HindIII fragment from pII3-1 into the HindIII site of either pHV3-2 or 6 is carried out to generate three recombinants designated pHHV3-31, 54 and 55. Fifth, pHHV3-31 and pBE0,514 are digested with EcoRI. Finally, sixth, the 1.0 kb EcoRI fragment from pHHV3-31 is inserted into the EcoRI site of pBE0,514. Nine identical recombinants, designated pGEX-PL 18C-31 to 39, are isolated by rabbit erythrocyte overlay.

More specifically, the 2.8 kb BstYI fragment of chromosomal DNA from S. pneumoniae type 18C described above is digested with HindIII and ligated into the BamHI and HindIII sites of pKK232-8 (19) as described (21) (FIG. 2 indicates the HindIII site). Competent cells (Stratagene Cloning Systems, La Jolla, Cailf.) of E. coli XL1-Blue (22) are transformed and plated on Luria-Bertani (LB) agar plates (21) containing ampicillin (50 µg/ml), with or without chloramphenicol (10 µg/ml). Ampicillin resistant transformants are screened by chloramphenicol resistance and colony hybridization (21) with a probe, 0.9 kb EcoRI-EcoRV fragment, which is derived from the type 20 ply gene (23). Among the several recombinants identified to contain the correct fragments, two designated pBH1-35 and pHB2-32 are selected to be used for the subcloning.

The complete ply gene is then constructed in pGEX-2T (20; available from Pharmacia LKB Biotechnology, Piscataway, N.J.) in frame to the 3' end of the gst gene by a conventional cloning method (21) and the polymerase chain reaction with Vent™ DNA polymerase (New England Biolabs, Beverly, Mass.). Competent cells (Stratagene) of E. coli SCS1 (24) are used. Ampicillin resistant tranformants are screened by rabbit erythrocyte overlay (12): colonies carrying recombinant plasmids show circular zones of hemolysis. One of nine isolates with similar characteristics, designated pGEX-PL 18C-31, is selected for further characterization (FIG. 2).

Expression, Purification and Characterization of rPL

The $pl_F$ gene from Type 18C/20 or 18C is cloned and over-expressed in E. coli as a glutathione S-transferase (GST) fusion protein (20). The resulting fusion protein is soluble in aqueous solutions and is purified from crude bacterial lysates under non-denaturing conditions. These conditions preserve the antigenicity of the rPL after purification. The GST-rPL fusion protein is able to be purified by simple means, such as affinity chromatography.

Figure 3:
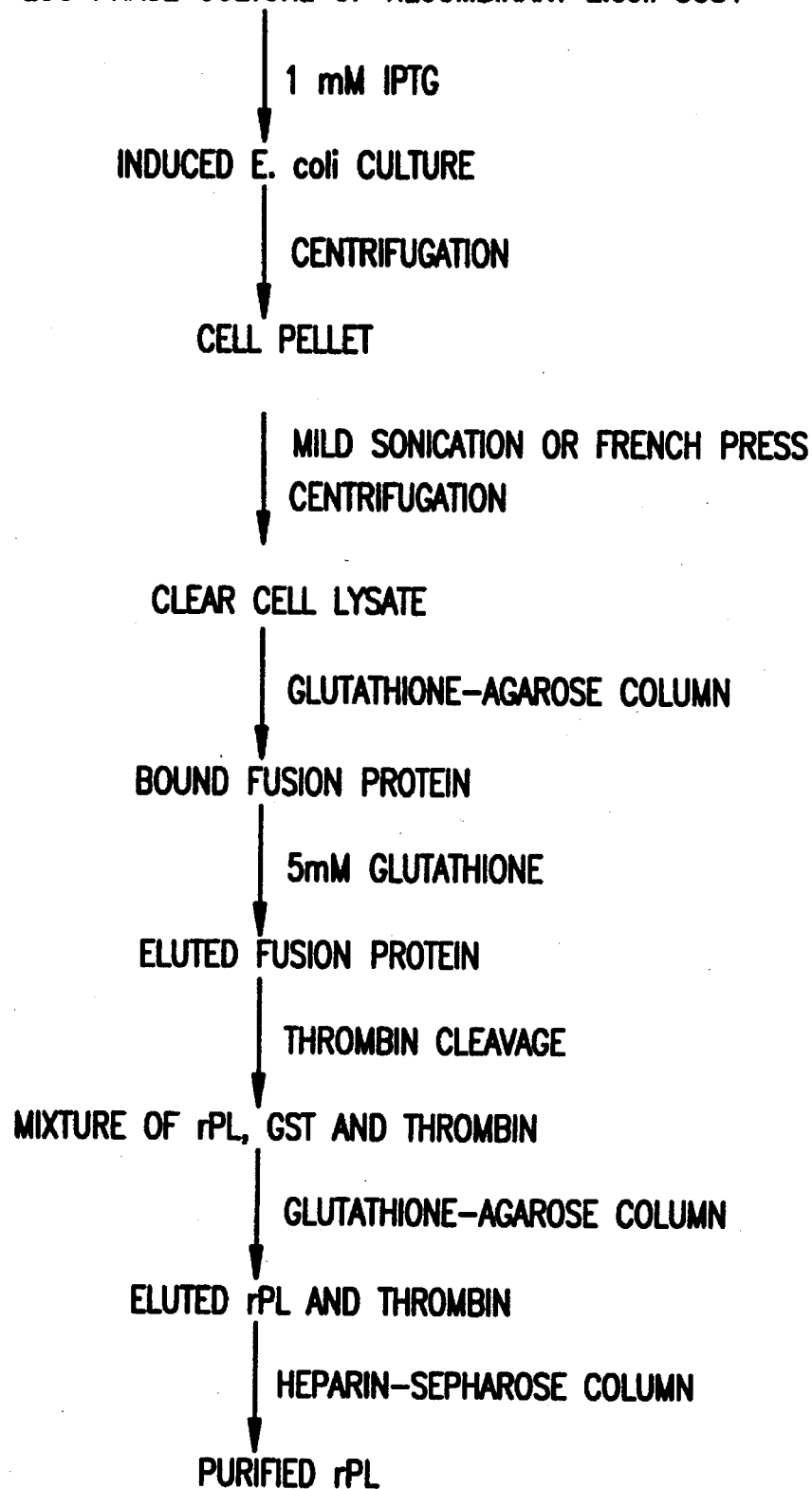
FIG. 3 depicts the method used to purify the recombinantly expressed rPL.
Figure 4A:
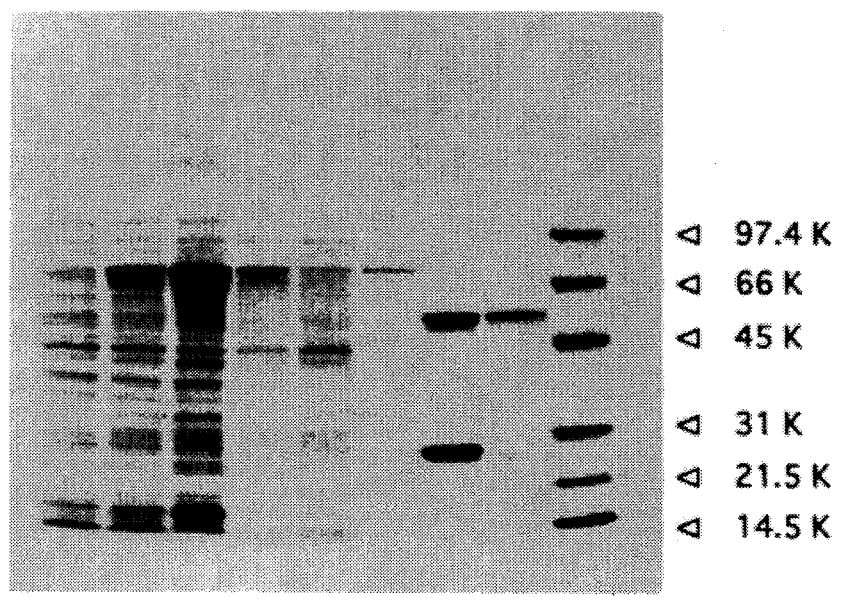
FIG. 4A depicts an SDS-PAGE (8–16% acrylamide stained with Coomassie blue) of rPL preparations at each step of purification. Lanes are as follows: 1. E. coli cells before IPTG induction, 2. E. coli cells after IPTG induction for 45 minutes, 3. E. coli cells after IPTG induction for 2 hours, 4. total cell lysate of induced E. coli, 5. E. coli proteins not bound by the affinity gel column (GST-rPL binds to the column), 6. purified fusion protein, GST-rPL, after elution, 7. mixture of GST and rPL after the thrombin digest of fusion protein, 8. purified rPL (free of GST and thrombin), 9. molecular markers (each in kD) as follows: 97.4-phosphorylase B; 66-bovine serum albumin; 45-ovalbumin; 31-carbonic anhydrase; 21.5-trypsin inhibitor; 14.5-lysozyme.
Figure 4B:
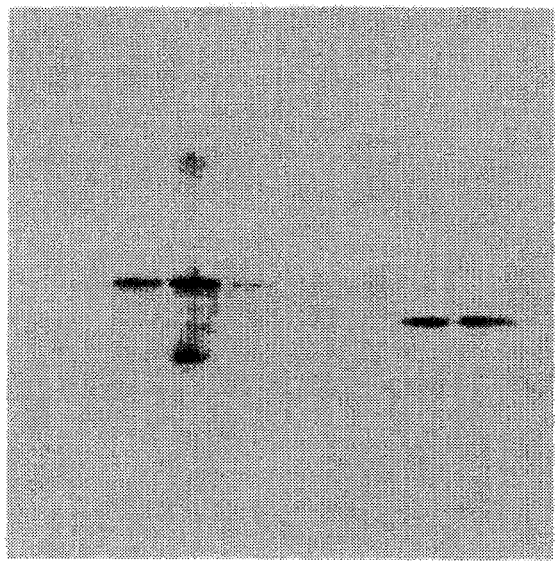
FIG. 4B depicts an immunoblot of rPL preparations at each step of purification. Rabbit antisera to native pneumolysin are used in inununoblotting. Lanes 1–8 correspond to Lanes 1–8 of FIG. 4A.

In order to purify a sufficient amount of rPn, the following affinity chromatography procedure is carried out. A flow diagram for the purification of rPL is shown in FIG. 3. An overnight culture of E. coli SCS1 containing either pGEX-PL 18C or pGEX-PL 18C/20 in 50 ml 1X Luria Broth or 1X Terrific Broth (25) containing ampicillin (100 µg/ml) is added to one liter of the same medium. Recombinant E. coli is then grown at 37° C. with vigorous shaking until an absorption of one at 600 run is reached. IPTG is added to the culture (to a concentration of 1 mM) as an inducer, and the E. coli cells are grown continuously for 2 hours. While a very small amount of the GST-rPL fusion protein is produced before induction (see lane 1, FIG. 4B), IPTG induces the expression of the fusion protein in large quantity within a short period of time (30 minutes to two hours). The fusion protein, GST-rPL, is over-expressed and comprises more than 10% of the total bacterial proteins on SDS-PAGE stained with Coomassie blue (FIG. 4).

Cells are centrifuged at 10,000×g for 5 or 10 minutes at 4° C., washed once with phosphate-buffered saline (PBS: 150 mMNaCl, 16 mM $NaH_2PO_4$, 4 mM $Na_2HPO_4$, pH 7.3), and resuspended in 1/50 volume of PBS. Triton X-100 is added to a 1% final concentration, and cells are lysed by mild sonication or two passages through a French Press (12,000 pounds). The lysate is centrifuged at 10,000×g for 10 minutes at 4° C., and cell debris is washed once with TPBS (1% Triton X-100 in PBS). Supernatants are pooled and 200 ml of clear cell lysate are applied to a column of 10 or 50 ml glutathione-agarose gel (Sigma Chemical Co., St. Louis, Mo.), equilibrated with TPBS. The column is washed with 5 bed-volumes of TPBS, 2 bed-volumes of PBS, and 1 bed-volume of 50 mM Tris-HCl, pH 8.0 to remove unwanted materials. The fusion protein, GSTrPL, is eluted with 5 or 10 mM glutathione/50 mM Tris-HCl, pH 8.0. Fractions showing hemolytic activity, as indicated by hemolytic and protein assays, are pooled. Fractions are identified as hemolytic as follows: One µl of each fraction is added to 50 µl of 10 mM DTT/PBS and then mixed on microtiter plates with 25 µl of 5% rabbit erythrocytes and incubated at room temperature for 15 minutes. Hemolysis is identified by eye.

GST-rPL is then digested by the protease, thrombin, which has a unique recognition site (20) between GST and rPL. The fusion protein is mixed with bovine plasma thrombin (Sigma) (5 units/mg protein) and then dialyzed (molecular weight cut-off: 12–14,000) against thrombin cleavage buffer (50 mM Tris-HCl, pH 8.3, 150 mM NaCl, 2.5 mM $CaCl_2$) at room temperature overnight. The mixture of GST, rPL and some undigested GST-rPL is centrifuged at 3,000×g at 20° C. using an Amicon Centriprep™-10 (Beverly, Mass.) (molecular weight cut-off: 10,000) to concentrate and exchange the buffer to PBS, and then applied onto the glutathione-agarose column. Because GST and any uncleaved GST-rPL bind specifically to the column, rPL passes freely through the column and is collected in the PBS eluate. Hemolytic fractions containing rPL are pooled. The buffer is exchanged to 10 mM sodium phosphate buffer (pH 7.0) using Centriprep™-10. Thrombin is removed from rPL (26) by passing through a column of 1 ml heparin-Sepharose™ gel (Pharmacia) equilibrated with 10 mM sodium phosphate buffer (pH 7.0). The purified rPL is stored at 4° C. The yield from this purification is approximately 6–10 mg/liter culture.

The purified rPn exhibits a single band on a gel with a molecular weight of 53,000 daltons as indicated by an SDS-PAGE/Coomassie blue stain. A densitometeric scan of the gel reveals that the purity of rPL is higher than 95%.

Although the method described above produces rPL of a purity greater than 95%, even higher purity can be obtained by adding a final step of hydroxylapatite (HA) chromatography. This step is performed using an HA-Fast Flow 1.6×8.0 cm column (Calbiochem. Corp., LaJolla, Calif.). The column is equilibrated with 10 mM sodium phosphate buffer (pH 6.8). A 10 ml (approximately 10 mg) portion of rPL is added to the HA column, and the protein eluted with a 100 ml linear gradient of 10 mM to 200 mM sodium phosphate buffer (pH 6.8). The column eluate is collected in 2.0 ml fractions at a flow rate of approximately 1.5 ml/min. Fractions are assayed as described previously (11). Fractions containing rPL are pooled and analyzed for protein concentration, hemolytic activity and purity by SDS-PAGE. The rPL is eluted as a single peak at approximately 85–115 mM phosphate buffer. The eluted protein is nearly homogeneous as shown by SDS-PAGE and is virtually free of contaminating lipopolysaccharide (endotoxin).

The molecular mass of rPL is 53,000 daltons as determined by SDS-PAGE and matrix assisted UV-laser desorption/ionization mass spectrometry.

The purified rPL has a specific activity of $3 \times 10^5$ hemolytic units/mg protein on rabbit erythrocytes (27), which is comparable to approximately $10^6$ hemolytic units/mg native PL (9,27). The specific hemolytic activity is determined by a slight modification of the method of Paton et al. (9). Samples are activated with 10 mM DTT before mixing with 1.7% rabbit erythrocytes. Absorbance of the supernatants is measured at 550 run.

In immunoblotting using Lumi-Phos™530 (Boehringer Mannheim Co., Indianapolis, Ind.) for chemiluminescence detection, both the GST-rPL fusion protein and rPL react with antisera containing the antibodies to native PL (FIG. 4B). Apparently, the higher molecular weight fusion protein is transferred to the Nytran membrane (Schleicher & Schuell Inc., Keene, N.H.) inefficiently compared to rPL and to breakdown products which can still be recognized by the antibodies. Ouchterlony immunodiffusion reveals that rPL reacts identically with anti-PL and anti-rPL antibodies. This suggests that rPL has the same antigenic determinants as native PL. Amino acid analysis and determination of the N-terminal sequence (up to 40 residues) are performed on the purified rPL. The N-terminal sequence of rPL is identical to that of the native PL and to the predicted sequence deduced from the nucleotide sequence of the type 2 ply gene (11,12), with the exception of two additional residues (glycine and serine), which remain on the rPL after thrombin cleavage at the N-terminus (20). The amino acid composition of rPL agrees well with that deduced from the nucleotide sequence of the type 2 ply gene (12).

Example 2

Preparation of *S. pneumoniae* Capsular Polysaccharide

The capsular polysaccharides of various pneumococcal types used in this invention have been described in commonly-assigned U.S. Pat. Nos. 4,242,501 (1) and 4,686,102 (3), which are incorporated by reference. The purified pneumococcal polysaccharides so obtained have a relatively high molecular size, with more than 50% having an elution coefficient ($K_{av}$) value less than 0.3 on a column of Sepharose™ CL-4B (Pharmacia LKB Biotechnology, Piscataway, N.J.). This value corresponds to a molecular weight greater than $6 \times 10^5$ daltons.

Example 3

Preparation Of Reactive Oxidized Type 14 Polysaccharide Containing Reducing Groups A 100 mg sample of pneumococcal Type 14 polysaccharide is dissolved in 20 ml of 0.1M sodium acetate buffer (pH 5.0). A 4 mg portion of sodium periodate (to a final concentration of 1 mM) is added in the dark and the mixture is stirred gently for 10 minutes at room temperature in a capped Erlenmeyer flask wrapped in aluminum foil. The excess sodium periodate is destroyed by reaction with 1 ml of 0.5 M ethylene glycol for 10 minutes at room temperature. The reactive mixture containing the resulting oxidized Type 14 ("[O]14") polysaccharide is extensively diafiltered and concentrated with an Amicon (Beverly, Mass.) concentrator with a 3,500 dalton cut-off membrane at room temperature. The diafiltered [O]14 polysaccharide is lyophilized and stored at −20° C. until used.

Example 4

Preparation Of Reactive Oxidized Type 18C Polysaccharide Containing Reducing Groups.

The procedure described in Example 3 for oxidizing the Type 14 polysaccharide is repeated for Type 18C, except that prior to periodate oxidation, the Type 18C polysaccharide is partially depolymerized by 1M acetic acid to prevent gelling of the polysaccharide when conjugated to rPL. A 500 mg sample of Type 18C polysaccharide is suspended in 50 ml acetic acid (final pH 2.5) and incubated at 60° C. for 40 hours. Then, 6 ml of 2M sodium acetate is added (final pH 4.0). The mixture is concentrated to approximately 12 ml using an Amicon stirred cell (YM10). The concentrate is subjected to column chromatography by placing on a Sepharose™ CL-4B column and eluting with 10mM PBS and 0.01% $NaN_3$. Fractions of 4 ml are collected and those at Kd 0.3–0.7 (10–60 kD) are pooled. The fractions are dialyzed against water with a 12–14 kD molecular weight cut-off, with water being changed daily. The periodate oxidation step is then performed to produce the oxidized Type 18C ("[O]18C") polysaccharide.

Example 5

Preparation of [O]14 Polysaccharide-rPL Conjugate

The [O]14 polysaccharide made in Example 3 is dissolved in 0.2M potassium phosphate buffer (pH 8.0) at a concentration of 6 mg/ml. The rPL made in accordance with Example 1 (expressed from either ATCC 69654 or ATCC 69655 in E. coli) is also dissolved in a separate container in the same buffer at a concentration of about 2 mg/ml. The [O]14 polysaccharide solution (0.5 ml) and the rPL solution (0.5 ml) are mixed at room temperature. After 30 minutes, sodium cyanoborohydride (2.5 mg) is added and the reaction mixture is incubated at room temperature for 5 days. The mixture is chromatographed on a column of Sepharose™ CL-4B, which is first equilibrated with 10 mM PBS (pH 7.0). The conjugate material is eluted with the same buffer without a gradient. Peak fractions containing the conjugate are assayed for polysaccharide and protein (15,17). The fractions which contain the conjugate are pooled, characterized and used for the vaccine preparations. The [O]14 polysaccharide-rPL conjugate has a carbohydrate/protein w/w ratio of about 7:1. The conjugate vaccine preparation is stored at 4° C. until used.

Example 6

Preparation Of [O]14 Polysaccharide-rPL Conjugate with the Spacer Adipic Acid Dihydrazide (ADH)

Preparation of rPL-ADH Derivative

Three ml of rPL (9 mg) made in accordance with Example 1 (either Type 18C or Type 18C/20) is placed in 0.1M potassium phosphate buffer (pH 5.5). The buffered rPL is mixed with ADH (20 mg) and carbodiimide (20 mg), and incubated at room temperature for 3 hours. The reaction mixture is changed to pH 7.0 by dialyzing against 0.1 M potassium phosphate buffer (pH 7.0) at 4° C in a Spectrapor membrane tubing with a 3,500 dalton cut-off membrane. The dialyzed material containing the rPL-ADH derivative is characterized by chromatography on a column of Sepharose™ CL-4B. The content of protein is assayed by the Bradford method (17), and ADH is measured by the 2,4,6-trinitrobenzenesulfonic acid reaction witbADE as a standard (28). The rPL-ADH derivative (a liquid) is stored at 4° C. until used.

Preparation of [O]14 Polysaccharide-ADH-rPL Conjugate

The [O]14 polysaccharide made in accordance with Example 3 is dissolved in 0.1M potassium phosphate buffer (pH 8.0) at a concentration of 6 mg/ml and the rPL-ADH derivative is also dissolved in a separate container in the same buffer at concentration of 3 mg/ml. A 2.5 ml sample of [O]14 polysaccharide and a 2.5 ml sample of the rPL-ADH derivative are mixed at room temperature. After 2 hours, sodium cyanoborohydride (12.5 mg) in water is added and the reaction mixture is incubated at 37° C. with gentle mixing for 4 days. The mixture is chromatographed on a column of Sepharose™ CL-4B which is first equilibrated with 10 mM PBS (pH 7.0). The conjugate material is eluted with the same buffer. Peak fractions containing the conjugate are identified as described above, and then are pooled, characterized and used for the vaccine preparations. Silver stained SDS-PAGE shows that high molecular weight material is present in the conjugate. A first group of pooled fractions designated pool 1 (from Sepharose™ CL-4B) conjugate has a $K_{av}$ of 0.08–0.20; while a second group of pooled fractions designated pool 2 contains material with a $K_{av}$ of 0.21–0.34. The ratio of carbohydrate:protein for the conjugate pool 1 is 11:1; the ratio for the conjugate pool 2 is 13:1. The conjugate preparations are used for the preparation of the vaccines. The conjugate preparations are stored at 4° C.

Example 7

Preparation of [O]18C Polysaccharide-rPL Conjugate

To prepare intermediate lengths of this polysaccharide suitable for conjugate use, a minor modification of the method of Example 4 is used. A 500 mg portion of type 18C polysaccharide is dissolved in 50 ml of 1M acetic acid (pH 2.3) and incubated at 60° C. for 40 hours. The treated polysaccharide is adjusted to pH 4.5 with 2M sodium acetate. The sample is molecular sized on a colualn of Sepharose™ CL-4B. The polysaccharide eluting at $K_{av}$ of 0.3 to 0.7 (mol. wt. 15,000–600,000) is pooled. The pooled fractions are extensively dialyzed against pyrogen-free water at 4° C. and then lyophilized. The material is stored at −20° C. until use for the preparation of the [O]18C polysaccharide.

A 50 mg portion of the intermediate size of the type 18C polysaccharide is dissolved in 10 ml of 0.1M sodium acetate buffer (pH 5.0) and oxidized with 4 mg of sodium periodate (final concentration 2 mM) in the dark for 10 minutes at room temperature. The excess sodium periodate is destroyed by reaction with 50 µl of 0.5M ethylene glycol (final concentration 25 mM) for 10 minutes. The reaction mixture containing [O]18C polysaccharide is extensively dialyzed and then lyophilized. The material is stored at −20° C. and used for the preparation of the conjugate with rPL.

The [O]18C polysaccharide is dissolved in 0.2M potassium phosphate buffer (pH 8.0) at a concentration of 6 mg/ml. The rPL made in accordance with Example 1 (expressed from either ATCC 69654 or ATCC 69655 in E. coli) is also dissolved in a separate container in the same buffer at a concentration of 3 mg/ml. One ml of [O]18C polysaccharide solution and 0.5 ml of the rPL solution are mixed at room temperature. After 1 hour, sodium cyanoborohydride (3 mg) is added and the reaction mixture is incubated at 37° C. for 8 days. The mixture is chromatographed on a column of Sepharose™ CL-4B, which is first equilibrated with 10 mM PBS (pH 7.0) and then eluted with the same buffer. Peak fractions containing the conjugate are identified as described above, pooled and characterized. The [O]18C polysaccharide-rPL conjugate has a carbohydrate/protein ratio of about 0.76:1. Silver stained SDS-PAGE shows that high molecular weight material is present. The

Example 8

Preparation of [O]18C Polysaccharide-rPL Conjugate with the Spacer ADH

Preparation of [O]18C polysaccharide

The [O]18C polysaccharide is prepared in accordance with Example 7, stored at −20° C. and used for the preparation of the conjugate with rPL-ADH derivative.

Preparation of rPL-ADH Derivative

A 10 ml portion of rPL (12 mg) made in accordance with Example 1 (either Type 18C or Type 18C/20) is placed in 0.1 M potassium phosphate buffer (pH 5.4). The buffered rPL is mixed with 0.3 ml ADH (30 mg) and 0.1 ml of carbodiimide (30 mg), and incubated with gentle mixing at room temperature for 3 hours. The reaction mixture is changed to pH 7.0 by dialyzing against 0.1M potassium phosphate buffer (pH 7.0) at 4° C for 2 days in a Spectrapor membrane tubing with a 3,500 dalton cut-off membrane. The dialyzed material containing the rPL-ADH derivative is concentrated to about 4 ml with an Amicon Centriprep™ (10,000 dalton cut-off) and is chromatographed on a column of Sepharose™ CL-4B. The content of protein and ADH are assayed as described previously. The rPL-ADH derivative is stored at 4° C. until used.

Preparation of [O]18C Polysaccharide-ADH-rPL Conjugate

The [O]18C polysaccharide is dissolved in 0.2M potassium phosphate buffer (pH 8.0) at a concentration of 6 mg/ml, and the rPL-ADH derivative is also dissolved in a separate container in the same buffer at a concentration of about 2.7 mg/ml. A 2.5 ml portion of [O]18C polysaccharide and 2.5 ml of the rPL-ADH derivative are mixed at room temperature. After 2 hours, sodium cyanoborohydride (12.5 mg) in water is added and the reaction mixture incubated at 37° C. with gentle mixing for 4 days. The mixture is chromatographed on a column of Sepharose™ CL-4B which is first equilibrated with 10 mM PBS (pH 7.0). The conjugate material is eluted with the same buffer. Peak fractions containing the conjugate are identified as described above, pooled, characterized and used for the vaccine preparations. Silver stained SDS-PAGE reveals high molecular weight materials present in the conjugate. The ratio of the [O]18C polysaccharide to rPL in the conjugate is about 1.8:1. The conjugate material is stored at 4° C.

Example 9

Antibody Response to the Conjugate Vaccines

The conjugates prepared by the procedures of the above Examples pass the general safety test in mice and guinea pigs required by the Food and Drug Administration (21 C.F.R. §610.11; Apr. 1, 1993). The conjugates are then tested for their ability to raise antibodies in mice. The conjugates are diluted in sterile PBS (pH 7.0) containing 0.01% thimerosal, such that a 0.2 ml dose contains 1 or 5 µg of the polysaccharide. The conjugate vaccines are sterilized by membrane filtration through a 0.2 µ Gelman filter. The sterile vaccine is stored at 4° C. until used.

CD-1 (Swiss) mice (8 weeks old) are injected intraperitoneally with 0.2 ml of the vaccine (1–5 µg per dose) absorbed onto aluminum phosphate (1 mg/ml) as an adjuvant. At 2 week intervals, the mice are Given two additional injections of the vaccine. Blood samples are collected by retro-orbital venipuncture two weeks after each injection. Seven mice are assayed by ELISA for the antibody titers to the polysaccharide and rPL. The results of the assay are depicted in Table 1 (for the [O]14/rPL conjugate) and Tables 2 and 3 (two separate experiments for the [O]18C/rPL conjugate):

TABLE 1

Antibody Responses to [O]14/rPL Conjugate Vaccines in Mice[a]

| Vaccine | Antibody Titers for S-14[b] | | | | Antibody Titers for rPL[c] | | | |
|---|---|---|---|---|---|---|---|---|
| | S-14 Dose (µg) | Week 2 | Week 4 | Week 6 | rPL Dose (µg) | Week 2 | Week 4 | Week 6 |
| rPL | — | <100 | <100 | <100 | 5 | 413 | 21085 | 182621 |
| [O]14 | 5 | <100 | — | <100 | — | <50 | <50 | 75 |
| [O]14-ADH | 5 | <100 | <100 | <100 | — | <50 | <50 | <50 |
| [O]14-rPL | 1 | <100 | 1232 | 2123 | 0.14 | 149 | 19854 | 41143 |
| [O]14-rPL | 5 | <100 | 4290 | 8320 | 0.71 | 1097 | 37578 | 96794 |
| [O]14-ADH-rPL(Pool 1)[d] | 1 | 4761 | >24300 | 343150 | 0.09 | <50 | 19757 | 127916 |
| [O]14-ADH-rPL(Pool 1) | 5 | 3875 | 166466 | 146560 | 0.46 | <50 | 7673 | 18407 |
| [O]14-ADH-rPL(Pool 2)[d] | 1 | >8100 | 575601 | 373790 | 0.08 | <50 | 14958 | 114360 |
| [O0]14-ADH-rPL(Pool 2) | 5 | 8597 | 425520 | 301492 | 0.39 | <50 | 30397 | 135534 |

[a]Groups of 5 Swiss mice (CD-1) are immunized three times (2 week intervals) with the vaccines.
[b]Pooled sera analyzed by ELISA. Titer represents endpoint = 0.1.
[c]Individual serum tested assayed by ELISA. GMT's represent endpoint = 0.3.
[d]The conjugate vaccine [O]14(ADH)rPL: Pool 1 Kd = 0.08–0.20, Pool 2 Kd = 0.21–0.34 (Sepharose ™ CL-4B).

TABLE 2

Antibody Responses to [O]18C/rPL Conjugate Vaccines in Mice

| Vaccine | Antibody Titers for S-18C | | | | Antibody Titers for rPL | | | |
|---|---|---|---|---|---|---|---|---|
| | S-18C* Dose (μg) | Week 2 | 4 | 6 | rPL** Dose (μg) | Week 2 | 4 | 6 |
| rPL | — | <100 | <100 | <100 | 1 | 207 | 87997 | 244285 |
| rPL | — | <100 | <100 | <100 | 5 | 2308 | 113104 | 409597 |
| [O]18C | 5 | <100 | <100 | <100 | — | <50 | <50 | <50 |
| [O]18C-rPL | 1 | <100 | <100 | 3909 | 1.39 | 366 | 7669 | 38792 |
| [O]18C-rPL | 5 | ~127 | 10417 | 13733 | 6.95 | 720 | 42072 | 83976 |
| [O]18C-ADH-rPL | 1 | <100 | 407 | 8004 | 0.69 | 747 | 34462 | 72881 |
| [O]18C-ADH-rPL | 5 | ~100 | ~157 | 2372 | 3.45 | 6353 | 232879 | 215029 |

Groups of 5 Swiss mice are immunized three times (2 weeks intervals) with the vaccines.
*Pooled sera analyzed by ELISA. Titer represents endpoint = 0.1
**Individual serum assayed by ELISA. GMT's represent endpoint = 0.3.

TABLE 3

Antibody Responses to [O]18C/rPL Conjugate Vaccines in Mice

| Vaccine | Antibody Titers for S-18C | | | | Antibody Titers for rPL | | | |
|---|---|---|---|---|---|---|---|---|
| | S-18C* Dose (μg) | Week 2 | 4 | 6 | rPL** Dose (μg) | Week 2 | 4 | 6 |
| rPL | — | <100 | <100 | <100 | 1 | 725 | 9904 | 374502 |
| [O]18C | 5 | <100 | <100 | <100 | — | <50 | <50 | 142 |
| [O]18C-rPL | 1 | <100 | 2432 | 9585 | 0.68 | 2506 | 63484 | 146113 |
| [O]18C-rPL | 5 | <100 | 240 | 1519 | 3.4 | 1447 | 34493 | 85675 |
| [O]18C-ADH-rPL | 1 | 168 | 8236 | 66763 | 0.49 | 552 | 1602 | 35478 |
| [O]18C-ADH-rPL | 5 | <100 | 2166 | 7420 | 2.43 | 621 | 15625 | 172614 |

Groups of 5 Swiss mice are immunized three times (2 weeks intervals) with the vaccines.
*Pooled sera analyzed by ELISA. Titer represents endpoint = 0.1
**Individual serum assayed by ELISA. GMT's represent endpoint = 0.3.

Example 10

Haemolytic Assay For Neutralizing Antibodies

A hemolytic assay for neutralizing antibodies is conducted as follows (9,12,29): In a 96-well (U-shaped) microtiter plate, dilutions of serum from animals (mice or rabbits) containing antibodies to rPL are mixed with 1 μg of rPL. After incubating for 15 minutes at 37° C., 10 mM dithiothreitol is added. After incubating for 15 minutes at 37° C., rabbit erythrocytes (1.7% final concentration) are added and incubated an additional 30 minutes in the same manner. After centrifugation at 150 ×g for 5 minutes, the presence or absence of pellets is noted. The dilution representing 50% lysis of erythrocytes is visually determined. If neutralizing antibodies are present, a pellet is seen; if no antibodies are present, the erythrocytes are lysed. The results of two hemolytic assays are I depicted in Tables 4 and 5:

TABLE 4

INHIBITION OF HEMOLYTIC ACTIVITY BY ANTI-rPL CONTAINING MOUSE SERA

| Antiserum (Immunized Vaccine) | [O]PS dose (μg) | Antibody titers* to Polysaccharides | rPL dose (μg) | Antibody Titers** to rPL | Neutralizing activity |
|---|---|---|---|---|---|
| [O]18C | 5 | <100 | — | <50 | — |
| rPL | — | <100 | 1 | 244285 | +1:16 |
| | — | <100 | 5 | 409597 | +1:16–32 |
| [O]18C-rPL | 1 | 3909 | 1.39 | 72881 | +1:8 |
| | 5 | 13733 | 6.95 | 215029 | +1:16 |
| [O]18C-ADH-rPL | 1 | 8004 | 0.69 | 38792 | +1:8 |
| | 5 | 2372 | 3.45 | 83976 | +1:8 |

*Pooled sera. Titer represents endpoint = 0.1.
**Individual serum. GMT's represent endpoint = 0.3.

TABLE 5

INHIBITION OF HEMOLYTIC ACTIVITY BY ANTI-rPL CONTAINING MOUSE SERA

| Antiserum (Immunized Vaccine) | [O]PS dose (μg) | Antibody titers* to Polysaccharides | rPL dose (μg) | Antibody Titers** to rPL | Neutralizing activity |
|---|---|---|---|---|---|
| [O]18C | 1 | <100 | — | — | — |
| rPL | — | <100 | 1 | 140025 | +1:32 |
| [O]18C-rPL, Pool 1*** | 0.2 | 163775 | 0.08 | 755 | +1:4 |
|  | 1.0 | 73919 | 0.42 | 53781 | +1:16 |
| [O]18C-rPL, Pool 2*** | 0.2 | 60479 | 0.05 | 2385 | +1:2-4 |
|  | 1.0 | 246599 | 0.25 | 34042 | +1:16 |
| [O]18C-rPL | 0.2 | 136897 | 0.09 | 13100 | +1:4 |
|  | 1.0 | 133575 | 0.42 | 26205 | +1:8 |

*Pooled sera. Titer represents endpoint = 0.1.
**Individual serum. GMT's represent endpoint = 0.3.
***Pool 1 Kd = 0.00–0.30; Pool 2 Kd = 0.30–0.60

Example 11

Endothelial Cell Cytotoxicity Assay

An endothelial cell cytotoxicity assay is performed according to the method of Rubins et al. (30). To radiolabel intact cells, the medium is removed after cells reach confluence, washed twice with PBS, trypsinized, washed twice with fresh culture medium, resuspended in 200 μl PBS and 300 μl $^{51}$Cr (300 μCi) and incubated at 37° C., 5% $CO_2$ for 90 minutes. Cells are washed twice in PBS containing 5% BSA and 2% dextrose and resuspended in PBS containing 0.5% BSA and 0.2% dextrose. Cells are adjusted to $2 \times 10^5$/ml. In a 96-well (U shaped) microtiter plate, dilutions of serum from animals (mice or rabbits) containing antibodies to rPL are mixed with 5 ng of rPL. After incubating for 15 minutes at 37° C., 5% $CO_2$, 10 mM dithiothreitol are added. After incubating for 30 minutes at 37° C., 5% $CO_2$, cells ($2 \times 10^4$) are added and incubated an additional 2 hours in the same manner. After centrifugation at 150×g for 3 minutes, the radioactivity in an aliquot of the supernatant is counted by liquid scintillation to determine the percent $^{51}$Cr released. In order to determine the remaining cellular $^{51}$Cr, 1N NaOH is added, the solution mixed, and the radioactivity in an aliquot counted. The percent $^{51}$Cr released is determined as the percentage of total counts per minute in the medium divided by the total counts per minutes in the medium and the cell layer. The results of the assay are depicted in Table 6, where the values refer to the mean and standard deviation from triplicate $^{51}$Cr-cell culture wells (24,000 cpm/200 μl ), $2 \times 10^4$ cells/well. The cells are incubated in the absence or presence of agent(s) as indicated for 2 hours at 37° C. in the presence of 10 mM dithiothreitol. The % $^{51}$Cr release =100×(2A/(A+B)); where A= cpm in top 100 μl; B= cpm in bottom 100 μl to which 100 μl NaOH is added.

TABLE 6

| Experimental Condition | Percent $^{51}$Cr Release |
|---|---|
| Total Counts | 97 ± 2.3 |
| Spontaneous Release | 9 ± 0.6 |
| rPL (5 ng) | 57 ± 0.6 |
| rPL + Anti-rPL Serum (1:1000) | 11 ± 1.2 |
| rPL + Anti-rPL Serum (1:2000) | 11 ± 1.0 |
| rPL + Anti-[O]18C Serum (1:1000) | 38 ± 1.2 |
| rPL + Anti-[O]18C Serum (1:2000) | 43 ± 1.5 |
| rPL + Anti-[O]18C rPL Serum (1:1000) | 11 ± 0.0 |

TABLE 6-continued

| Experimental Condition | Percent $^{51}$Cr Release |
|---|---|
| rPL + Anti-[O]18C rPL Serum (1:2000) | 11 ± 0.6 |
| rPL + Anti-[O]18C-ADH-rPL Serum (1:1000) | 11 ± 0.0 |
| rPL + Anti-[O]18C-ADH-rPL Serum (1:2000) | 11 ± 0.6 |

Example 12

Protection Against Challenge with Live S. pneumoniae in Mice Vaccinated with rPL or Conjugated Vaccines Female, eight week old CD-1 mice in groups of ten are injected intraperitoneally with 0.2 ml of various vaccines at two week intervals. These vaccines included rPL, [O]18C-rPL and [O]18C-ADH-rPL. The control vaccine, [O]18C, does not induce an antibody response in these mice. Each mouse is injected with a vaccine dose containing 1 μg of polysaccharide, or in the case of vaccine containing only rPn, 1 μg of protein. All vaccines also contain 1 mg/ml aluminum phosphate. Sera from representative mice are collected prior to initial vaccination and at 2 and 4 weeks post initial vaccination. Sera from all mice is collected 11 days after the last vaccination. The sera are used to determine the antibodies against rPL and [O]18C. Two weeks after the last vaccination, the mice are injected with varying doses of S. pneumoniae, type 18C (ATCC 6318). The bacteria are grown overnight on Trypticase™ Soy Agar with 5% sheep blood plates (BBL, Cockeysville, Md.; trademark of Beeton, Dickinson and Co.) overnight at 37° C., then inoculated into Trypticase™ Soy Broth (TSB) (BBL; trademark of Becton, Dickinson and Co.) containing 5% defibrinated sheep blood and 1% glucose and incubated unshaken at 37° C. for six hours. The growth is diluted appropriately with TSB. The number of CFU/ml is determined by plate count. The doses of bacteria injected intraperitoneally are calculated to be approximately 0, 5, 25, 125 and 625×$LD_{50}$, where $LD_{50}$ is less than or equal to 3 CFU/dose. Thus, the bacterial doses are 0, 23, 115, 575 and 2875 CFU/dose. The animals are checked twice a day and any deaths are recorded.

The results are shown in Table 7. All mice serving as negative controls receiving TSB but no bacteria are alive and well after 14 days. All mice vaccinated with [O]18C, the positive control which does not induce an antibody response, die within four days after challenge with any of the four doses of *S. pneumoniae*. Mice receiving rPL vaccine alone, which does induce significant antibody responses to rPL, survive for a longer time than the positive controls. The conjuate vaccines of this invention, containing [O]18C and rPL either with or without a spacer, when given before bacterial challenge are the most effective in protecting mice against lethal infection by Type 18C pneumococci, even with the highest challenge dose of $2.9 \times 10^3$ CFU ($625 \times$ $LD_{50}$). These conjugate vaccines also elicit significant antibody responses to both the Type 18C polysaccharide and rPL (see Tables 2 and 3).

Conf. on Streptococcal Genetics, A/43, Minneapolis, Minn. (1989).

13A. Taira, S., et al., *Gene*, 77, 211–218 (1989).

14. Parikh, I., et al., *Methods Enzymol.*, 34, 77–102 (1974).

15. DuBois, M., et al., *Anal. Chem.*, 28, 350–356 (1956).

16. Schwartz, B. A., and Gray, G. R., *Arch. Biochem. Biophys.*, 181., 542–549 (1977).

17. Bradford, M. M., *Anal. Biochem.*, 72, 248–254 (1976).

18. U.S. Pat. No. 5,057,540.

19. Brosius, J., *Gene*, 27, 151–160 (1984).

TABLE 7

Effect of Vaccination with rPL and Conjugate Vaccines on Survival of Mice Challenged with *S. pneumoniae*
Number of Mice Dead (Total mice = 10/group)[c]

| Vaccine[a] | Organisms[b] $LD_{50}$ | Live (CFU/dose) | 1 | 2 | 3 | 4 | 5 | 6 | 7 | 8 | 9 | 10 | 11 | 12 | 13 | 14 | Final |
|---|---|---|---|---|---|---|---|---|---|---|---|---|---|---|---|---|---|
| rPL | 0X | (0) | 0 | 0 | 0 | 0 | 0 | 0 | 0 | 0 | 0 | 0 | 0 | 0 | 0 | 0 | 0 |
| (1 µg rPL/dose) | 5X | (23) | 0 | 1 | 4 | 2 | 1 | 0 | 1 | 0 | 0 | 0 | 0 | 0 | 1 | — | 10 |
| | 25X | (115) | 0 | 1 | 4 | 2 | 1 | 0 | 0 | 2 | — | — | — | — | — | — | 10 |
| | 125X | (575) | 0 | 4 | 3 | 0 | 0 | 1 | 0 | 2 | — | — | — | — | — | — | 10 |
| | 625X | (2875) | 0 | 1 | 2 | 0 | 1 | 2 | 1 | 2 | 0 | 0 | 0 | 1 | — | — | 10 |
| [O]18C-rPL | 0X | (0) | 0 | 0 | 0 | 0 | 0 | 0 | 0 | 0 | 0 | 0 | 0 | 0 | 0 | 0 | 0 |
| (1 µg [O]18C/dose) | 5X | (23) | 0 | 1 | 0 | 0 | 0 | 0 | 0 | 0 | 0 | 0 | 0 | 0 | 0 | 0 | 1 |
| | 25X | (115) | 0 | 0 | 0 | 1 | 0 | 0 | 0 | 0 | 0 | 1 | 0 | 0 | 0 | 0 | 2 |
| | 125X | (575) | 0 | 1 | 1 | 1 | 0 | 0 | 0 | 0 | 0 | 0 | 0 | 0 | 0 | 0 | 3 |
| | 625X | (2875) | 0 | 0 | 1 | 0 | 0 | 1 | 0 | 0 | 0 | 0 | 0 | 0 | 0 | 0 | 2 |
| [O]18C-ADH-rPL | 0X | (0) | 0 | 0 | 0 | 0 | 0 | 0 | 0 | 0 | 0 | 0 | 0 | 0 | 0 | 0 | 0 |
| (1 µg [O]18C/dose) | 5X | (23) | 0 | 0 | 0 | 0 | 0 | 0 | 0 | 0 | 0 | 0 | 0 | 0 | 0 | 0 | 0 |
| | 25X | (115) | 0 | 0 | 0 | 0 | 0 | 0 | 0 | 0 | 0 | 0 | 0 | 0 | 0 | 0 | 0 |
| | 125X | (575) | 0 | 0 | 0 | 0 | 1 | 0 | 0 | 0 | 0 | 0 | 0 | 0 | 0 | 0 | 1 |
| | 625X | (2875) | 0 | 0 | 0 | 0 | 0 | 0 | 0 | 0 | 0 | 0 | 0 | 1 | 0 | 0 | 1 |
| [O]18C | 0X | (0) | 0 | 0 | 0 | 0 | 0 | 0 | 0 | 0 | 0 | 0 | 0 | 0 | 0 | 0 | 0 |
| (1 µg [O]18C/dose) | 5X | (23) | 0 | 7 | 2 | 1 | — | — | — | — | — | — | — | — | — | — | 10 |
| | 25X | (115) | 1 | 5 | 2 | 2 | — | — | — | — | — | — | — | — | — | — | 10 |
| | 125X | (575) | 2 | 2 | 5 | 1 | — | — | — | — | — | — | — | — | — | — | 10 |
| | 625X | (2875) | 0 | 3 | 3 | 4 | — | — | — | — | — | — | — | — | — | — | 10 |

[a]The vaccines in a dose of 1 µg polysaccharide for the conjugates or 1 µg rPL for the rPL preparation are given 3 times on days 1, 14, and 28.
[b]The live organisms, type 18C *S. pneumonias* (ATCC 6318) in varying doses are inoculated IP on day 42.
[c]Mice are observed for up to 14 days after challenge.

Bibliography

1. U.S. Pat. No. 4,242,501.

2. U.S. Pat. No. 4,221,906.

3. U.S. Pat. No. 4,686,102.

4. U.S. Pat. No. 4,673,574.

5. Paton, J. C., Published International patent application no. WO 90/06951.

6. Paton, J. C., *Infect. Immun.*, 59, 2297–2304 (1991).

7. Lee, C.-J., et al., *Vaccine*, 12, 875–878 (1994).

8. Boulnois, G. J., *J. Gen. Microbiol.*, 138, 249–259 (1992).

9. Paton, J. C., et al., *Infect. Immun.*, 40, 548–552 (1983).

10. Bailey, et al., Program Abstr. 1987 Intersci. Conf., *Antimicrob. Agents Chemother.*, Abstr. 895 (1987).

11. Paton, J. C., et al., *Infect. Immun.*, 54, 50–55 (1986).

12. Walker, J. A., et al., *Infect. Immun.*, 55, 1184–1189 (1987).

13. Li, J. P., et al., Immunochemical characterization of group 19 pneumolysins and molecular cloning of 19F pneumolysin gene, Presented at the 3rd Intl. Am. Microbiol.

20. Smith, D. B., and Johnson, K. S., *Gene*, 67, 31–40 (1988).

21. Sambrook, J., et al., Molecular Cloning: a laboratory manual, Cold Spring Harbor Laboratory, Cold Spring Harbor, N.Y. (1989).

22. Bullock, W. O., et al., *Biotechniques*, 5, 376–378 (1987).

23. Ree, H. K., et al., Cloning of the pneumolysin gene from *Streptococcus pneumoniae*; Over-expression in *Escherichia coli* as a fusion protein for simple purification, Presented at ASM 93rd General Meeting. Atlanta, Ga. (1993).

24. Hanahan, D., *J. Mol. Biol.*, 166, 557–(1983).

25. Tartof, K. D., and Hobbs, C. A., *Bethesda Res. Lab. Focus*, 9, 12 (1987).

26. Bajaj, S. P., et al., *Prep. Biochem.*, 11, 397–412 (1981).

27. Kanclerski, K., and Mollby, R., *J. Clinical Microbiol.*, 25, 222–225 (1987).

28. Inman, J. K., et al., *Biochemistry*, 8, 4074–4080 (1969).

29. Difco Manual, Streptolysin O Reagents, p. 889 (Difco Labs).

30. Rubins, J. B., et al., *Infection and Immunity*, 60, 1740–1746 (1992).

What is claimed is:

1. An immunogenic polysaccharide-protein conjugate obtained by reductive amination comprising (a) an oxidized polysaccharide derived from the capsular polysaccharide of *Streptococcal pneumoniae* (*S. pneumoniae*), and (b) the pneumolysin protein of *S. pneumoniae* which is expressed recombinantly, where said pneumolysin is not toxoided or is not produced by site-specific mutagenesis prior to conjugation with said oxidized polysaccharide.

2. The conjugate of claim 1, wherein the capsular polysaccharide of *S. pneumoniae* is derived from Type 14 or Type 18C.

3. The conjugate of claim 2, wherein the capsular polysaccharide of *S. pneumoniae* is derived from Type 18C.

4. The conjugate of claim 1, wherein the pneumolysin which is expressed recombinantly is expressed in *E. coli*.

5. The conjugate of claim 4, wherein the pneumolysin which is expressed recombinantly is expressed in the *E. coli* strain designated SCS1.

6. The conjugate of claim 5, wherein the pneumolysin which is expressed recombinantly is expressed in the *E. coli* strain designated SCS1, which harbors a plasmid selected from the group consisting of the plasmid designated pGEX-PL 18C (ATCC 69654) and the plasmid designated pGEX-PL 18C/20 (ATCC 69655).

7. The conjugate of claim 6, wherein the pneumolysin which is expressed recombinantly is expressed in the *E. coli* strain designated SCS1, which harbors a plasmid designated pGEX-PL 18C (ATCC 69654).

8. The conjugate of claim 6, wherein the pneumolysin which is expressed recombinantly is expressed in the *E. coli* strain designated SCS1, which harbors a plasmid designated pGEX-PL 18C/20 (ATCC 69655).

9. The conjugate of claim 1, wherein the recombinantly-expressed pneumolysin is first linked to a spacer prior to conjugation with the oxidized polysaccharide derived from the capsular polysaccharide of *S. pneumoniae*.

10. The conjugate of claim 9, wherein the spacer is selected from the group consisting of adipic acid dihydrazide (ADH) and 6-aminocaproic acid.

11. The conjugate of claim 10, wherein the spacer is ADH.

12. A vaccine comprising an immunogenic polysaccharide-protein conjugate obtained by reductive amination comprising (a) an oxidized polysaccharide derived from the capsular polysaccharide of *S. pneumoniae*, and (b) the pneumolysin protein of *S. pneumonias* which is expressed recombinantly, where said pneumolysin is not toxoided or is not produced by site-specific mutagenesis prior to conjugation with said oxidized polysaccharide.

13. The vaccine of claim 12 which further comprises one or more of an immunologically acceptable diluent, carrier or adjuvant.

14. The vaccine of claim 12 which comprises a mixture of at least two immunogenic conjugates with oxidized polysaccharides derived from capsular polysaccharides of different types of *S. pneumoniae*.

15. A method of eliciting an antibody response to the capsular polysaccharide of *S. pneumoniae* in warm-blooded animals, which comprises adminstering to said animals an immunogenic amount of the vaccine of claim 14.

16. A method of immunizing against *S. pneumonias*-caused disease in warm-blooded animals, which comprises administering to said animals the vaccine of claim 14 in an immunogenic amount by intramuscular, intraperitoneal or subcutaneous injection.

* * * * *